United States Patent [19]

Olney

[11] Patent Number: 5,011,853
[45] Date of Patent: Apr. 30, 1991

[54] COMPOUNDS FOR TREATMENT OF CHOLINERGIC NEUROTOXINS

[75] Inventor: John W. Olney, Ladue, Mo.

[73] Assignee: Washington University, St. Louis, Mo.

[21] Appl. No.: 470,825

[22] Filed: Jan. 26, 1990

Related U.S. Application Data

[63] Continuation-in-part of Ser. No. 398,721, Aug. 25, 1989.

[51] Int. Cl.⁵ ..................... A01N 43/16; A61K 31/35
[52] U.S. Cl. ................................. 514/454; 546/127; 546/128; 546/203; 560/58; 514/456; 514/534
[58] Field of Search ............... 546/203, 128, 127, 133; 514/397, 454, 299, 318, 456, 334; 560/58; 424/10

[56] References Cited

U.S. PATENT DOCUMENTS 4,945,097 7/1990 Olney .................................. 514/318

OTHER PUBLICATIONS

Niemegeers et al., Archives Internationales de Pharmacodynamie et de Therapie, vol. 259, pp. 153-165, 1982.
Jovic et al., Chemical Abstract, vol. 73, p. 236, 1970, 118907m.
Lin et al., Chemical Abstract, vol. 110, p. 235, 1989, 187,417.
McLeod, C. G. et al., "Acute Neuropathology in Soman-Poisoned Rats", *Neurotoxicology* 5: 53-58 (1984).
Olney, J. W., "Excitatory Transmitters and Epilepsy-Related Brain Damage", *Intl. Rev. Neurobiol.* 27: 337-362 (1985).
Clifford, D. B. et al., "The Functional Anatomy and Pathology of Lithium-Pilocarpine and High-Dose Pilocarpine Seizures", *Neurosci.* 23: 953-968 (1987).
Olney, J. W. et al., "Anti-Parkinsonian Agents Are Phencyclidine Agonists and N-Methyl Aspartate Antagonists", *Eur. J. Pharmacol.* 142: 319-320 (1987).
Shih, T. M. et al., "Studies of Potential Anticonvulsants in Soman Poisoning", *Soc. for Neurosci. Abstr.* 15: 623 (1989).
Stitcher et al., "Effect of Pyridostigmine and Cholinolytics on Cholinesterase and Acetylcholine in Soman-Poisoned Rats", *Drug and Chemical Toxicology* 1(4): 355-362 (1978).
Pazdernik et al., "Effects of Antidotes on Soman-Induced Brain Changes", *Arch. Toxicol., Suppl.* 9: 333-336 (1986).
Dunn, M. A. and Sidell, F., "Progress in Medical Defense Against Nerve Agents", *J. Amer. Med. Assn.* 262(5): 649-652 (1989).
Stryer, L., *Biochemistry*, 2nd Edition, pp. 890-893 (Freeman and Company, San Francisco).

*Primary Examiner*—Jose G. Dees
*Assistant Examiner*—Deborah D. Carr
*Attorney, Agent, or Firm*—Haverstock, Garrett and Roberts

[57] ABSTRACT

This invention discloses the use of muscarinic anti-cholinergic agents for reducing or preventing the toxic or lethal effects (such as seizures and brain damage) caused by cholinergic neurotoxins. The parent application disclosed that certain muscarinic anti-cholinergics classified as aryl-cycloalkyl-alkanolamines are effective in reducing or preventing the neurotoxicity of soman, a powerful nerve gas. This invention extends that discovery and identifies other muscarinic anti-cholinergic agents, including scopolamine, benactyzine, and benztropine, as highly effective and useful agents to protect against two major classes of cholinergic neurotoxins (acetylcholine receptor agonists, and cholinesterase inhibitors). Analogs of those compounds may also be effective in protecting against cholinergic neurotoxicity, as can be determined through routine screening tests using rats. It has been discovered that protection against seizures induced by lithium and pilocarpine (drugs that are widely available and used frequently in research) provides a good indicator of effectiveness against soman, a nerve gas which is heavily restricted and extremely dangerous.

18 Claims, No Drawings

COMPOUNDS FOR TREATMENT OF CHOLINERGIC NEUROTOXINS

RELATED APPLICATION

This application is a continuation-in-part of U.S. Pat. application Ser. No. 398,721, filed on Aug. 25, 1989.

FIELD OF THE INVENTION

This invention is in the fields of pharmacology and neurology. It relates specifically to compounds and methods for reducing the neurotoxic effects of cholinergic agents.

BACKGROUND OF THE INVENTION

The background of the invention is discussed in the parent application Ser. No. 398,721, which was invented by the same inventor and is assigned to the same assignee. The contents of that patent application are incorporated herein by reference.

The parent application describes the toxic and lethal effects of cholinergic neurotoxins such as pilocarpine, an experimental drug which is of interest to researchers studying the causes and mechanisms of epilepsy (Clifford et al 1987; complete citations are provided below), and soman, a nerve gas that poses a threat in chemical warfare (McLeod et al 1984). Either of those substances can cause continuous seizure activity which persists for hours and causes disseminated brain damage, which typically is fatal unless adequately treated. The parent application discloses that a class of compounds referred to as aryl-cycloalkyl-alkanolamines are effective in protecting lab animals against convulsions or death when they are exposed to soman, even when the aryl-cycloalkyl-alkanolamines are administered only after the onset of seizure activity. Those compounds have a biological activity which can be classified as muscarinic anti-cholinergic activity, since they antagonize (i.e, inhibit the activation or effects of) the muscarine class of acetylcholine receptors on the surfaces of neurons in the central nervous system. Aryl-cycloaklyl-alkanolamine drugs include procyclidine, biperiden, triperiden, and trihexyphenidyl.

The subject invention discloses that a number of other muscarinic anti-cholinergics which do not fall within the aryl-cycloalkyl-alkanolamine class of compounds have also been determined to be effective against cholinotoxic syndromes.

SUMMARY OF THE INVENTION

This invention discloses the use of muscarinic anti-cholinergic agents for reducing or preventing the toxic or lethal effects (such as seizures and brain damage) caused by cholinergic neurotoxins. The parent application disclosed that certain muscarinic anti-cholinergics classified as aryl-cycloalkyl-alkanolamines are effective in reducing or preventing the neurotoxicity of soman, a powerful nerve gas. This invention extends that discovery and identifies other muscarinic anti-cholinergic agents, including scopolamine, benactyzine, and benztropine, as highly effective and useful agents to protect against two major classes of cholinergic neurotoxins (acetylcholine receptor agonists, and cholinesterase inhibitors). Analogs of those compounds may also be effective in protecting against cholinergic neurotoxicity, as can be determined through routine screening tests using rats. It has been discovered that protection against seizures induced by lithium and pilocarpine (drugs that are widely available and used frequently in research) provides a good indicator of effectiveness against soman, a nerve gas which is heavily restricted and extremely dangerous.

DESCRIPTION OF THE PREFERRED EMBODIMENTS

This invention relates to compounds and methods for reducing neurotoxic effects (such as seizures and brain damage) caused by cholinergic agents such as soman (a nerve gas). Effective treatment can be provided by administering scopolamine, benactyzine, or benztropine. Table 1 provides an index of the effectiveness of these three agents against lithium-pilocarpine seizures. These data were gathered as described in Example 1.

TABLE 1

| PROTECTION AGAINST LITHIUM-PILOCARPINE SEIZURES | |
|---|---|
| DRUG | $ED_{50}$ (mg/kg) |
| Scopolamine | 0.93 |
| Trihexyphenidyl | 2.5 |
| Benactyzine | 4.2 |
| Biperiden | 4.5 |
| Benztropine | 4.5 |
| Procyclidine | 8.3 |
| Atropine | 22.9 |

The $ED_{50}$ refers to the dosage (in milligrams of drug per kilogram of body weight) that was effective in preventing seizure activity and neurotoxic damage (based on histologic examination) in 50% of the rats treated with lithium and pilocarpine. For comparative purposes, Table 1 contains data on several other protective agents. Three of those agents (trihexyphenidyl, biperiden, and procyclidine) belong within the class of aryl-cycloalkyl-alkanolamine compounds described in the above-cited parent application. The last agent, atropine, is listed to show the weakness of its protective effects.

Shih et al 1989, which is not regarded as prior art, describes the attempted evaluation of a variety of compounds as potential protective agents against soman. Those agents include a variety of sedatives and tranquilizers, several "tertiary anti-cholinergics" including scopolamine and benztropine, and various other compounds. However, the test methods used in those studies did not clearly reveal the utility of scopolamine or any other compounds as useful protective agents, for several reasons. Shih et al co-administered an additional protective agent (a cholinesterase reactivator, oxime HI-6) to the test animals in order to try to offset the effects of soman, which is a cholinesterase inactivator. In addition, Shih administered the potential protective agents to the animals 30 minutes prior to the administration of soman; that type of prior administration would be unavailable in most cases where needed, such as an emergency response to the symptoms of poisoning, or a reaction to a nerve gas attack. In addition, Shih et al did not perform electroencephalographic measurements; instead, they only observed externally manifested convulsive symptoms such as tremors. This led to misleading or uninterpretable results, since convulsive activity was probably masked and was not externally displayed despite convulsive activity inside the brain when various agents such as sedatives, tranquilizers, or NMDA antagonists were used. Shih et al also did not examine the brains histologically to determine whether any of the agents they tested effectively prevented damage inside the brain.

As mentioned above, Shih et al 1989 is not regarded as prior art. Prior to its appearance in October 1989, the inventor had already discovered that one class of muscarinic anti-cholinergics (aryl-cycloalkyl-alkanolamines) were effective in protecting against cholinergic neurotoxicity. Subsequently, the inventor was engaged in other research which indicated that scopolamine, benztropine, benactyzine, and aryl-cycloalkyl-alkanolamines were all effective in preventing adverse side effects caused by NMDA antagonists, including vacuole formation and mitochondrial dissolution in cingulate/-retrosplenial neurons. Based on their common activity as muscarinic anti-cholinergics, the inventor realized that scopolamine, benztropine, benactyzine, and other muscarinic anti-cholinergics outside the aryl-cycloalkyl-alkanolamine class probably would also be effective in protecting against soman neurotoxicity. He soon proved that to be the case, using the methodology he had already developed and used to select, breed, and test a soman-sensitive colony of rats using procyclidine.

Regardless of whether Shih et al 1989 is regarded as prior art, the subject invention discloses for the first time that the compounds disclosed herein provide effective protection against cholinergic neurotoxins without requiring (1) pretreatment before exposure to the cholinergic neurotoxin, or (2) co-administration of other protective agents.

Structurally, scopolamine is highly similar to atropine. They differ by a single oxygen atom, as follows:

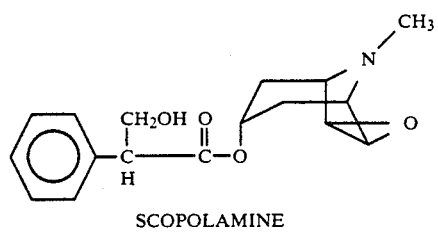

SCOPOLAMINE

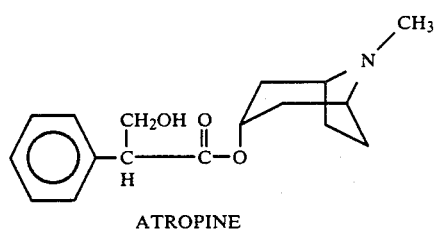

ATROPINE

It was previously known that atropine provides a limited degree of protection against seizures induced by pilocarpine, if the atropine is administered prior to the pilocarpine (Honchar et al 1983). Since the protection provided by atropine is low, its was surprising that scopolamine provides a very high degree of protection. This result indicates that a high degree of blockage of M1 muscarinic receptors is valuable in protecting against cholinotoxic damage. Data on M1 and M2 affinities (derived from Freedman et al 1988, page 136) are listed in Table 2. That correlation, although potentially helpful, is not complete, as evidenced by a comparison of trihexyphenidyl and benztropine in Tables 1 and 2.

TABLE 2

RELATIVE AFFINITIES OF VARIOUS COMPOUNDS FOR M1 AND M2 RECEPTORS

| COMPOUND | $1/K_{app}$ M1 (brain) | $1/K_{app}$ M2 (heart) | M1/M2 RATIO |
|---|---|---|---|
| Scopolamine | 2.17 | 0.20 | 11.1 |
| Benztropine | 1.14 | 0.07 | 18.0 |
| Biperiden | 0.83 | 0.04 | 18.0 |
| Atropine | 0.63 | 0.29 | 2.1 |
| Trihexyphenidyl HCl | 0.45 | 0.03 | 13.0 |

Source:
Freedman et al, Eur. J. Pharmacology 156: 133 at 136 (1988)

Various other muscarinic anti-cholinergics, including analogs of the compounds listed above, may also be effective in protecting against pilocarpine or soman toxicity, as can be determined through routine screening tests (as described in the Examples) to assess the effectiveness of any specific analog against cholinergic toxins such as pilocarpine or soman.

"Analog" is used herein in its conventional pharmaceutical sense, to refer to pharmaceutical agents that are structurally related to a specific compound and differ by a limited number of alterations. For example, methyl or other alkyl or aryl groups may be added at certain locations on the molecule; halogen moieties (such as chloride groups) can be added, unsaturated bonds may be substituted in place of saturated bonds, an ether linkage may be added to a ring structure, and other such changes may be made using techniques known to chemists who specialize in pharmacological synthesis, to create a variety of analogs based on scopolamine, benactyzine, benztropine, or any other muscarinic anti-cholinergic agent.

An important aspect of this invention is the discovery that a simple assay, which evaluates protection against a seizure/brain damage syndrome induced by combined treatment with lithium and pilocarpine, provides a good indicator of effectiveness against soman, a nerve gas which is heavily restricted and extremely dangerous. This discovery allows analogs of scopolamine, benactyzine, benztropine, or other muscarinic anti-cholinergics to be screened simply and inexpensively for protective effects against cholinergic neurotoxins, using lithium and pilocarpine, which are used frequently in research.

Although pilocarpine and soman are both cholinergic neurotoxins (they both cause toxic overstimulation of acetylcholine receptors on the surfaces of neurons in the central nervous system), they work through completely different mechanisms. Pilocarpine is an acetylcholine receptor agonist; it binds to and activates acetylcholine receptors. By contrast, soman is a cholinesterase inhibitor; it inactivates the enzyme that normally degrades extracellular acetylcholine. By inactivating that enzyme, soman leads to a toxic buildup of acetylcholine. As used herein, the term "cholinergic neurotoxin" refers to both of those classes of compounds (acetylcholine receptor agonists, and cholinesterase inhibitors).

The protective agents disclosed herein can "reduce or prevent" the neurotoxic effects of cholinergic neurotoxins. The phrase "reduce or prevent" is used broadly; it includes any degree of reduction, mitigation, or prevention of one or more adverse effects. It also includes the use of the neuroprotective compounds described herein on a precautionary basis. For example, the use of these protective agents to safeguard workers who must clean out a storage facility that once held a pesticidal cholinesterase inhibitor, or the use of these protective agents to safeguard soldiers or civilians against a possible nerve gas attack, are included within the meaning of the phrase "reduce or prevent".

Included within the family of protective compounds disclosed herein are therapeutically effective tautomers or isomers of the described compounds, as well as pharmaceutically-acceptable salts thereof. The term "pharmaceutically-acceptable salts" embraces salts commonly used to form alkali metal salts and to form addition salts of free acids or free bases. Since the compounds disclosed herein contain basic nitrogen atoms, such salts are typically acid addition salts. The nature of the salt is not critical, provided that it is pharmaceutically acceptable, and acids which may be employed to form such salts are well known to those skilled in this art. Examples of acids which may be employed to form pharmaceutically acceptable acid addition salts include such inorganic acids as hydrochloric acid, sulphuric acid and phosphoric acid, and organic acids such as maleic acid, succinic acid and citric acid. Other salts include salt with alkali metals or alkaline earth metals, such as sodium, potassium, calcium and magnesium.

Administration of the compounds disclosed herein to humans can be by any technique capable of introducing the compounds into the bloodstream of a human patient, including oral administration, and by intravenous, intramuscular and subcutaneous injections. The active compound is usually administered in a pharmaceutically-acceptable formulation, although in some acute-care situations a compound described herein may be administered alone. Such formulations may comprise the active compound together with one or more pharmaceutically acceptable carriers or diluents. Other therapeutic agents may also be present in the formulation. A pharmaceutically acceptable carrier or diluent provides an appropriate vehicle for delivery of the active compound without introducing undesirable side effects.

EXAMPLES

Example 1

Lithium-pilocarpine assay using post-treatment

Adult male Sprague Dawley rats (300-400 g) were treated with lithium chloride (3 meq/kg subcutaneous (sc)), to potentiate the pilocarpine effect and reduce individual variability among the rats. Twenty four hours later, they received an injection of pilocarpine (30 mg/kg ip). The animals were observed until they began to convulse, then were given one of the test agents listed in Table 1 (or saline, for control purposes) and observed for an additional 4 hours. Various dosages of the protective agents were administered to different groups of rats (n=at least 4 in each group) in order to calculate, by linear regression analysis, an $ED_{50}$ (i.e., the dosage effective in protecting 50% of the treated animals). After 4 hours, the animals were deeply anesthetized and sacrificed by perfusion of fixative through the heart and ascending aorta into the brain. The brains were evaluated for histopathological changes as described in Olney 1971.

All of the rats in the saline control group (i.e., rats that received lithium/pilocarpine but no protective agent) displayed the full behavioral syndrome of pre-convulsive and convulsive symptoms with persistent seizure activity being present for the majority of the 4 hour observation period.

During the observation period, electroencephalographic measurements were taken of rats treated with procyclidine, to determine whether that particular muscarinic anti-cholinergic protected against lithium-pilocarpine (or against soman, as described in Example 2). Those studies confirmed that (1) major EEG abnormalities were present in all animals that suffered external symptoms when treated with either convulsive agent, and (2) the muscarinic anti-cholinergic agent used (procyclidine) completely blocked EEG-recordable seizure activity for the entire 4 hour observation period.

After the observation period ended, the rats were sacrificed, and histological examination revealed that all rats which suffered seizure activity had severe brain damage affecting the cerebral cortex, hippocampus, amygdala, piriform cortex, thalamus, lateral septum and substantia nigra. By contrast, rats whose initial seizure activity was treated using a muscarinic anti-cholinergic agent had no significant damage.

All of the agents listed in Table 1 provided protection against the lithium-pilocarpine cholinotoxic syndrome, as evidenced behaviorally by the fact that the rats stopped seizing within 5 to 10 minutes after administration of an effective dose of the drug and remained free of seizure activity for the rest the observation period. Such animals did not display any histopathological brain damage.

Example 2

Soman assay using post-treatment

A major problem in studying the soman cholinotoxic syndrome is the marked individual variation in sensitivity of experimental animals. Some adult rats develop status epilepticus (persistent seizures) within 5 to 15 minutes after receiving a dose of soman in the range of 90 to 125 ug/kg (micrograms/kilogram) ip. Those animals typically sustain severe brain damage and die within 1 to 6 hours. However, other rats can tolerate much higher doses of soman without exhibiting seizures or brain damage and such animals survive treatment without any apparent untoward effects. Administering lithium chloride 24 hours prior to soman causes a moderate, but consistent, increase in the percentage of animals susceptible to soman neurotoxicity.

In a study to evaluate procyclidine as a protective agent against the neurotoxic effects of soman (as described in the parent application), adult male Sprague Dawley rats (350-425 g) were pretreated with lithium chloride (3 mg/kg sc) and 24 hrs later given soman (125 ug/kg sc) and observed for symptoms. Animals that began convulsing were treated immediately either with saline (control group) or a single dose (75 mg/kg ip) of procyclidine (treatment group). In that study, it was shown that procyclidine provided effective protection against the seizure/brain damage syndrome induced by soman.

The neuroprotective properties of procyclidine were then exploited to establish a colony of rats selectively bred for increased susceptibility to soman neurotoxicity. Adult male and female rats were challenged with soman. Those that responded with seizures (n=8) were identified as soman-sensitive and were treated with procyclidine which protected them, allowing them to survive and serve as breeding stock. The first generation offspring of soman-sensitive male/female matings were challenged with soman and found to have a substantially increased rate of soman sensitivity (increased from 40% to 80%), even though lithium pretreatment was not used.

Additional offspring from the soman-sensitive colony were used to test the protective agents listed in Table 1, to determine their effectiveness in preventing damage from soman. Since only a small number of animals were available, the test groups were not large enough to provide reliable statistical data in those preliminary tests. However, those preliminary results made it clear that protection against lithium-pilocarpine seizures is a valid indicator of protective capability against soman. The compounds listed in Table 1 provided varying degrees of protection against soman, and their relative rankings were comparable (i.e, scopolamine provided the highest degree of protection, while trihexyphenidyl came next, followed by benactyzine, biperiden, and benztropine). In general, the amount of a protective agent necessary to provide effective protection against soman was several times higher than the amount required to protect against lithium-pilocarpine; this is consistent with the fact that soman is a long-lasting cholinesterase inhibitor, while pilocarpine is an acetylcholine agonist that is metabolized fairly quickly.

Although this invention has been described with respect to specific embodiments, the details of these embodiments are not to be construed as limitations. Various equivalents and modifications may be made without departing from the spirit and scope of this invention, which is limited only by the claims which follow.

REFERENCES

Clifford D.B., et al, "The functional anatomy and pathology of lithium-pilocarpine and high-dose pilocarpine seizures," *Neurosci.* 23: 953-968 (1987).

Freedman et al, *Eur. J. Pharmacology* 156: 133 (1988).

Honchar, M.P., Olney, J.W. and Sherman, W.R., "Systemic cholinergic agents induce seizures and brain damage in lithium-treated rats," *Science* 220: 323-325 (1983).

McLeod, C.G., et al, "Acute neuropathology in soman-poisoned rats," *Neurotoxicology* 5: 53-58 (1984).

Olney, J. W., "Glutamate-induced neuronal necrosis in the infant mouse hypothalamus: an electron microscopic study," *J. Neuropathol. Exp. Neurol.* 30: 75-90 (1971).

Shih, T.M., et al, "Studies of potential anti-convulsants in soman poisoning," *Soc. for Neurosci. Abstr.* 15: 623 (1989)

I claim:

1. A method for reducing or preventing neurotoxicity, comprising administering to a susceptible mammal a therapeutically effective amount of a muscarinic anti-cholinergic agent which readily penetrates the blood-brain barrier and which has an M1/M2 receptor affinity ratio that is substantially higher than the affinity ratio of atropine for such receptors, wherein the muscarinic anti-cholinergic agent reduces or prevent the neurotoxic brain damage that would otherwise be caused by a cholinergic neurotoxin.

2. The method of claim 1, wherein the muscarinic anti-cholinergic agent is selected from the group consisting of scopolamine, benactyzine, and benztropine.

3. The method of claim 1, wherein the cholinergic neurotoxin comprises of cholinesterase inhibitor.

4. The method of claim 3, wherein the cholinesterase inhibitor comprises soman.

5. The method of claim 1, wherein the cholinergic neurotoxin comprises an acetylcholine receptor agonist that preferentially activates M1 muscarinic receptors.

6. A method for reducing or preventing neurotoxicity, comprising administering to a susceptible mammal a therapeutically effective amount of a compound comprising scopolamine or an analog thereof which readily penetrates the blood-brain barrier and which has an M1/M2 receptor affinity ratio that is substantially higher than the affinity ratio of atropine for such receptors, wherein the compound reduces or prevents the neurotoxic effects of a cholinergic neurotoxin.

7. The method of claim 6, wherein the cholinergic neurotoxin comprises a cholinesterase inhibitor.

8. The method of claim 7, wherein the cholinesterase inhibitor comprises soman.

9. The method of claim 6, wherein the cholinergic neurotoxin comprises an acetylcholine receptor agonist that preferentially activates M1 muscarinic receptors.

10. A method for reducing or preventing neurotoxicity, comprising administering to a susceptible mammal a therapeutically effective amount of a compound comprising benactyzine or an analog thereof which readily penetrates the blood-brain barrier and which has an M1/M2 receptor affinity ratio that is substantially higher than the affinity ratio of atropine for such receptors, wherein the compound reduces or prevents the neurotoxic effects of a cholinergic neurotoxin.

11. The method of claim 10, wherein the cholinergic neurotoxin comprises a cholinesterase inhibitor.

12. The method of claim 11, wherein the cholinesterase inhibitor comprises soman.

13. The method of claim 10, wherein the cholinergic neurotoxin comprises an acetylcholine receptor agonist that preferentially activates M1 muscarinic receptors.

14. A method for reducing or preventing neurotoxicity, comprising administering to a susceptible mammal a therapeutically effective amount of a compound comprising benztropine or an analog thereof which readily penetrates the blood-brain barrier and which has an M1/M2 receptor affinity ratio that is substantially higher than the affinity ratio of atropine for such receptors, wherein the compound reduces or prevents the neurotoxic effects of a cholinergic neurotoxin.

15. The method of claim 14, wherein the cholinergic neurotoxin comprises a cholinesterase inhibitor.

16. The method of claim 15, wherein the cholinesterase inhibitor comprises soman.

17. The method of claim 14, wherein the cholinergic neurotoxin comprises an acetylcholine receptor agonist that preferentially activates M1 muscarinic receptors.

18. An article of manufacture comprising packaging material and a pharmaceutical agent contained within said packaging material, wherein said pharmaceutical agent is effective for reducing the neurotoxicity of at least one cholinergic neurotoxin, and wherein said packaging material comprises a label which indicates that said pharmaceutical agent can be used for reducing the neurotoxicity of at least one cholinergic neurotoxin, and wherein said pharmaceutical agent is selected from the group consisting of scopolamine, benactyzine, and benztropine, and analogs thereof which readily penetrate the blood-brain barrier and which have an M1/M2 receptor affinity ratio that is substantially higher than the affinity ratio of atropine for such receptors.

* * * * *